United States Patent [19]

Paspek, Jr. et al.

[11] 4,161,613

[45] Jul. 17, 1979

[54] RECOVERY OF ACRYLIC ACID FROM QUENCH BOTTOMS BY THE ADDITION OF ALUMINUM CHLORIDE

[75] Inventors: Stephen C. Paspek, Jr., Cleveland; William A. Every, Twinsburg, both of Ohio

[73] Assignee: Standard Oil Company (Ohio), Cleveland, Ohio

[21] Appl. No.: 860,516

[22] Filed: Dec. 14, 1977

[51] Int. Cl.$^2$ .................. C07C 51/42; C07C 57/04
[52] U.S. Cl. .................................................. 562/600
[58] Field of Search ................... 260/526 N; 562/600

[56] References Cited

U.S. PATENT DOCUMENTS 3,663,375  5/1972  Witheford ........................ 260/540

*Primary Examiner*—Vivian Garner
*Attorney, Agent, or Firm*—David J. Untener; Herbert D. Knudsen; Larry W. Evans

[57] ABSTRACT

The addition of a salt comprising a group III A metal halide, such as aluminum chloride, to an acrylic acid-water solution obtained from the oxidation of propylene or acrolein, allows recovery of a 95% or better acrylic acid solution by phase separation.

12 Claims, No Drawings

RECOVERY OF ACRYLIC ACID FROM QUENCH BOTTOMS BY THE ADDITION OF ALUMINUM CHLORIDE

BACKGROUND OF THE INVENTION

A gaseous reactor effluent containing acrylic acid, acetic acid, water and various organic impurities is obtained by the oxidation of propylene or acrolein over an oxidation catalyst. This gas stream is then condensed or absorbed in water to obtain an aqueous solution of acrylic acid, acetic acid and water.

The concentration of acrylic acid in this solution varies. In a fixed-bed reactor, where diluents such as steam may be used, a final aqueous solution of about 10 wt.% acrylic acid is obtained. Where diluents are not used, the resulting aqueous solution can contain about 30–70 wt.% acrylic acid.

Because of the relative volatilities of acrylic acid and water, simple distillation is extremely difficult. Therefore, many different methods of recovery of acrylic acid have been proposed. For example, U.S. Pat. No. 3,816,524 discloses the use of various solvents to extract acrylic acid. The extraction is then followed by stripping the solvent from the acrylic acid in a distillation column.

Another method of recovery is azeotropic distillation. U.S. Pat. No. 3,830,707 discloses a process wherein a specific entrainer of isooctane or nitroethane is used to perform the distillation.

Both of these methods have various drawbacks. Distillation even under vacuum involves subjecting the acrylic acid to temperatures that usually cause some polymerization of the acid. Solvent extraction requires many columns, a high solvent to feed ratio, and suffers high solvent losses.

A variation on solvent extraction is by the addition of certain salts such as sodium chloride to accelerate phase separation after extraction, as shown in U.S. Pat. No. 3,846,488.

Other specific salts have been used for various purposes. U.S. Pat. No. 3,663,375 describes a process for salting out organics such as methacrylic acid using electrolytes such as sodium sulfate. These salts have not been effective for acrylic acid however, due to the difference in structure between the acids.

Finally, U.S. Pat. No. 2,922,815 discloses that drying agents such as calcium chloride can be used to obtain a 50–60% acrylic acid solution; dry metal salts such as nickel chloride or nickel bromide can obtain concentrations of up to 80% acrylic acid; and that it is not possible to obtain higher concentrations in this manner.

The present invention, through the use of specific salts, allows concentrations of between 90–100% acrylic acid to be obtained by phase separation at very desirable temperatures.

SUMMARY OF THE INVENTION

The invention may be stated as being a method of obtaining high purity acrylic acid from an aqueous solution of acrylic acid and water, e.g., an aqueous mixture containing 40–80 wt.% acrylic acid, comprising adding a salt comprising a group III A metal halide to said aqueous solution in an amount sufficient to form an organic phase and an aqueous phase, and separating the organic phase from the aqueous phase.

The above method can produce a concentration of greater than 95 volume % of acrylic acid in the organic phase. This method of separation can then be repeated to obtain higher purities of acrylic acid.

The salt should consist of a group III A metal halide, being boron, aluminum, gallium, indium, or thallium halide. It is preferred that the metal be aluminum, and it is preferred that the metal halide be aluminum chloride. The salt can be in the pure form, anhydrous, or in the form of a hydrate.

Upon addition of the salt, the aqueous solution should be well mixed. This mixing increases the contacting efficiency, thereby increasing the amount of acrylic acid that is separated. Centrifugation will also aid in phase separation.

The amount of salt added should be sufficient to saturate the aqueous solution. Experiments have indicated that approximately 10–15 wt.% of aluminum chloride anhydrate is required to saturate a 50 wt.% acrylic acid solution. The recovery efficiency of the acid declines rapidly with salt concentrations below the saturation level.

An important advantage of using the above salts to recover acrylic acid is that the operating temperature is much lower than found in the distillation process. Distillation requires high temperatures which lead to polymerization of the acid. In the present invention, however, using aluminum chloride salt for example, temperatures of from 25° C. to about 80° C. are preferred, with 25° C. to 50° C. being most preferred. Operations below 25° C. hinder the separation process, while temperatures higher than 50° C. result in only minor improvements in recovery.

After mixing, the aqueous solution containing acrylic acid can be passed to a decanter where phase separation takes place. It has been discovered that 95% recovery of acrylic acid with a purity of 99% can be obtained with a single stage of separation using an aluminum chloride salt.

The organic phase typically contains very low levels of salt, usually less than 0.1 wt.%. This salt can be removed by subsequent processing of the organic phase which also removes any organic impurities contained therein.

When using aluminum chloride as the salt, the aqueous phase will contain approximately 30 wt.% aluminum chloride and about 5 wt.% acrylic acid, with the remainder being water.

This phase should then be treated to recover the aluminum chloride for reuse. Virtually all the aluminum chloride can be recovered by the introduction of gaseous HCl to the aqueous phase. It has been found that over 98 wt.% of the aluminum chloride can be precipitated from this phase with the addition of 40 wt.% HCl at 25° C. Lower temperatures further improve this recovery. The remaining HCl solution can be further treated by such known methods as drying with $H_2SO_4$ or calcium chloride to recover and reuse the HCl.

It has also been found that the acrylic acid contained in the aqueous phase can also be recovered by further addition of aluminum chloride, heating the aqueous phase to a temperature of 50°–80° C., e.g., to about 60° C., and then cooling to room temperature. Because of the large amount of aluminum chloride contained in this phase, super saturation will occur, and approximately 25% of the acrylic acid contained in this phase will separate at about a 90% purity.

Organic contaminates such as acetic acid have little effect on the separation process. Acetic acid will divide between the phases, with more being present in the aqueous phase. It is preferred however, that the amount of acrolein in the effluent be below 2 wt.%, preferably less than 1 wt.%. Acrolein concentrations greater than 1 wt.% will effect the separation capabilities of the salts, specifically aluminum chloride.

EXAMPLES 1-5

Approximately 50 milliliters of a feed solution consisting of acrylic acid and water was saturated with aluminum chloride. For Example 1, the mixture was allowed to separate into phases without mixing. For Examples 2-5 the solution was mixed for one hour at constant temperature using a heated magnetic stirrer. The mixture was then centrifuged for 0.5 hours. Centrifugation was accomplished at a temperature between 25°-40° C. by utilizing an infrared heat lamp. The phases were then allowed to separate, and each phase was analyzed for acrylic acid. The results are shown in the following table.

TABLE I

Acrylic Acid Recovery Using $AlCl_3 \cdot 6 H_2O$

| | | Vol. % Acrylic Acid | | |
|---|---|---|---|---|
| Example | Temp. | Feed | Organic Phase | Aqueous Phase |
| 1* | 25° C. | 52 | 89 | 9 |
| 2 | 0° C. | 52 | 81 | 13 |
| 3 | 25° C. | 53 | 97.5 | 6.6 |
| 4 | 50° C. | 53 | 98.1 | 6.0 |
| 5 | 75° C. | 53 | ~100 | 8.5 |

As shown by the table above, acrylic acid can be obtained at exceptionally high purity by using the present invention.

We claim:

1. A process for the separation of acrylic acid from an aqueous mixture of acrylic acid and water comprising adding a Group III A metal halide salt to said aqueous mixture in an amount sufficient to form an organic phase containing acrylic acid, and an aqueous phase, and separating the organic phase from the aqueous phase.

2. The process of claim 1 wherein the Group III A metal is boron.

3. The process of claim 1 wherein the aqueous mixture contains 40-80 wt.% acrylic acid.

4. The process of claim 1 wherein the aqueous mixture containing the salt is mixed prior to separation.

5. The process of claim 1 wherein the Group III A metal is aluminum.

6. The process of claim 5 wherein the salt is aluminum chloride.

7. The process of claim 6 wherein the aqueous mixture containing aluminum chloride is at a temperature of 25° C. to about 80° C.

8. The process of claim 7 wherein the temperature is 25° C. to 50° C.

9. The process of claim 6 wherein the aqueous phase after separation from the organic phase is heated to a temperature of 50°-80° C. with further salt addition, and then cooled to a temperature wherein a second organic phase is produced.

10. The process of claim 6 wherein the aqueous phase containing aluminum chloride and water is contacted with HCl sufficient to cause precipitation of the aluminum chloride.

11. The process of claim 6 wherein the aqueous mixture additionally contains less than 1 wt.% acrolein.

12. The process of claim 6 wherein the salt is in the hydrated form.

* * * * *